(12) United States Patent
Yang

(10) Patent No.: US 7,625,357 B2
(45) Date of Patent: Dec. 1, 2009

(54) SAFETY WINGED NEEDLE STRUCTURE

(76) Inventor: Chang-Ming Yang, No. 27, Guangfu Rd., Junan Jen, Miaoli (TW)

( * ) Notice: Subject to any disclaimer, the term of this patent is extended or adjusted under 35 U.S.C. 154(b) by 0 days.

(21) Appl. No.: 11/763,289

(22) Filed: Jun. 14, 2007

(65) Prior Publication Data

US 2007/0233014 A1 Oct. 4, 2007

Related U.S. Application Data

(63) Continuation-in-part of application No. 10/673,983, filed on Sep. 30, 2003, now abandoned.

(51) Int. Cl.
*A61M 5/32* (2006.01)
(52) U.S. Cl. .................. 604/198; 604/177
(58) Field of Classification Search .......... 604/110, 604/165.01–165.04, 177, 187, 192, 197, 604/198, 263
See application file for complete search history.

(56) References Cited

U.S. PATENT DOCUMENTS

| | | | | |
|---|---|---|---|---|
| 4,170,993 A | * | 10/1979 | Alvarez | 604/180 |
| 4,834,708 A | * | 5/1989 | Pillari | 604/165.04 |
| 4,941,881 A | * | 7/1990 | Masters et al. | 604/162 |
| 5,498,241 A | * | 3/1996 | Fabozzi | 604/177 |
| 5,501,672 A | * | 3/1996 | Firth et al. | 604/177 |
| 6,659,984 B2 | * | 12/2003 | Crawford et al. | 604/263 |
| 6,743,186 B2 | * | 6/2004 | Crawford et al. | 600/583 |

* cited by examiner

*Primary Examiner*—Nicholas D Lucchesi
*Assistant Examiner*—Theodore J Stigell
(74) *Attorney, Agent, or Firm*—Banger Shia

(57) ABSTRACT

A safety winged needle structure includes a protective casing, at least one sliding slot disposed on the protective casing, and having a first position where the needle is shielded and a second position where the needle is exposed, two wings extended from both sides of the sliding slot, and one wing has the first positioning portion; an accommodating body, having sliding member disposed at the sliding slot, a neck portion and the top of the neck portion is a pushing portion. The second positioning portion disposed on pushing portion; and a needle connected to the sliding member; so that when the sliding member is moved to the second position, both wings are lifted and folded, so the first positioning portion behind the second positioning portion at its posterior part is fixed as well as the sliding member can not be withdrawn.

3 Claims, 8 Drawing Sheets

SAFETY WINGED NEEDLE STRUCTURE

RELATED APPLICATIONS

This application is a continuation-in-part of U.S. patent application Ser. No. 10/673,983, filed on Sep. 30, 2003 now abandoned.

FIELD OF THE INVENTION

The present invention relates to a safety winged needle structure, and more particularly to a safety winged needle structure that can be operated easily and safely without worrying about a sliding needle or an unintentional contact of the tip of the needle.

BACKGROUND OF THE INVENTION

In general, a prior art winged needle structure is composed of a needle assembly and a needle cover, wherein the needle assembly includes a plurality of wings extended from a lateral side of the body of the needle assembly and an injection needle inserted into a front end of the needle assembly, and the needle cover is in a cylindrical shape and includes an accommodating hole disposed at the bottom of the needle cover. In the method and structure of protecting an injector of the aforementioned prior art winged needle, it is necessary to remove the needle body from the needle cover and insert the injection needle into a desired injecting position of a patient for an injection, and then reattach the needle cover to the needle body after its use, and thus medical professionals may prick their fingers that hold the needle cover and get infected easily.

To overcome the foregoing shortcoming, a general prior art winged needle usually cancels the design of the needle cover and adopts a winged needle having a safety needle cover instead, wherein a wing is extended horizontally from each lateral side of the winged needle, and an injection needle is inserted into a front end of the winged needle, and the safety needle cover is a hollow cylindrical body, so that the winged needle can be slid in the safety needle cover. If a user wants to use the winged needle, the user needs to push the winged needle to the front end of the safety cover to expose the injection needle, and then fold the wings on both lateral sides of the winged needle, and hold the two wings by a hand for the injection or medical treatment. After the safety winged needle is used, the winged needle is retracted, so that the point of the injection needle enters into the safety needle cover. Medical professionals are required to complete the aforementioned operating procedure by one hand, so as to prevent them from being pricked or infected by the injection needle.

However, one of the drawbacks of the foregoing structure resides on that both winged needle and safety needle cover are sliding components, such that when a medical professional inserts the injection needle into a patient's skin by holding the two wings of the injection needle for the patient's medical treatment, the winged needle often slides backwards due to the resistance of the needle, and thus causing medical malpractice and negligence easily. Another drawback of the foregoing structure resides on that the safety cover is a cylindrical body, and medical professionals are required to complete the injection for medical treatment by one hand. During the process of pushing or retracting the winged needle, medical professionals use their thumb and middle finger to clamp and hold the safety cover, and use their index finger to push the winged needle. If the clamping is not secured, the whole set of winged needle may fall out or cause potential risks during the process of pushing or retracting the winged needle.

In view of the foregoing shortcomings of the prior art, the inventor of the present invention based on years of experience in the related industry to conduct extensive researches and experiments to overcome the shortcomings of the prior art, and finally developed a safety winged needle structure in accordance with the present invention.

SUMMARY OF THE INVENTION

The present invention is to provide a safety winged needle structure to improve the prior art winged needle that will slide backwards due to the resistance and cause inconvenience to users, and also provide an easy-to-grab holding portion to assure that the user's fingers can securely hold the cylindrical body and operate the needle by one hand.

The present invention provides a safety winged needle structure, comprising: a protective casing, a sliding slot disposed on a sidewall of the protective casing and extended from an end of the protective casing to another end of the protective casing, and sequentially having a first position and a second position, two wings extended separately from both sides of the sliding slot to the sidewall of the protective casing, and at least one wing has the first positioning portion; an accommodating body, disposed in the protective casing, and having a sliding member slidably disposed on the sliding slot, a neck portion and a pushing portion, and a second positioning portion disposed on the pushing portion; and a needle inserted into an end of the accommodating body. In the foregoing structure, the two wings are folded onto both sides of the sliding slot when the sliding member is moved along the sliding slot to the second position where the needle is exposed, so that the first positioning portion of the wing blocks the corresponding second positioning portions of the pushing portion at its posterior part for positioning the sliding member.

To make it easier for our examiner to understand the objective of the invention, its structure, innovative features, and performance, we use a preferred embodiment together with the attached drawings for the detailed description of the invention.

DETAILED DESCRIPTION OF THE PREFERRED EMBODIMENTS

Figure 1:
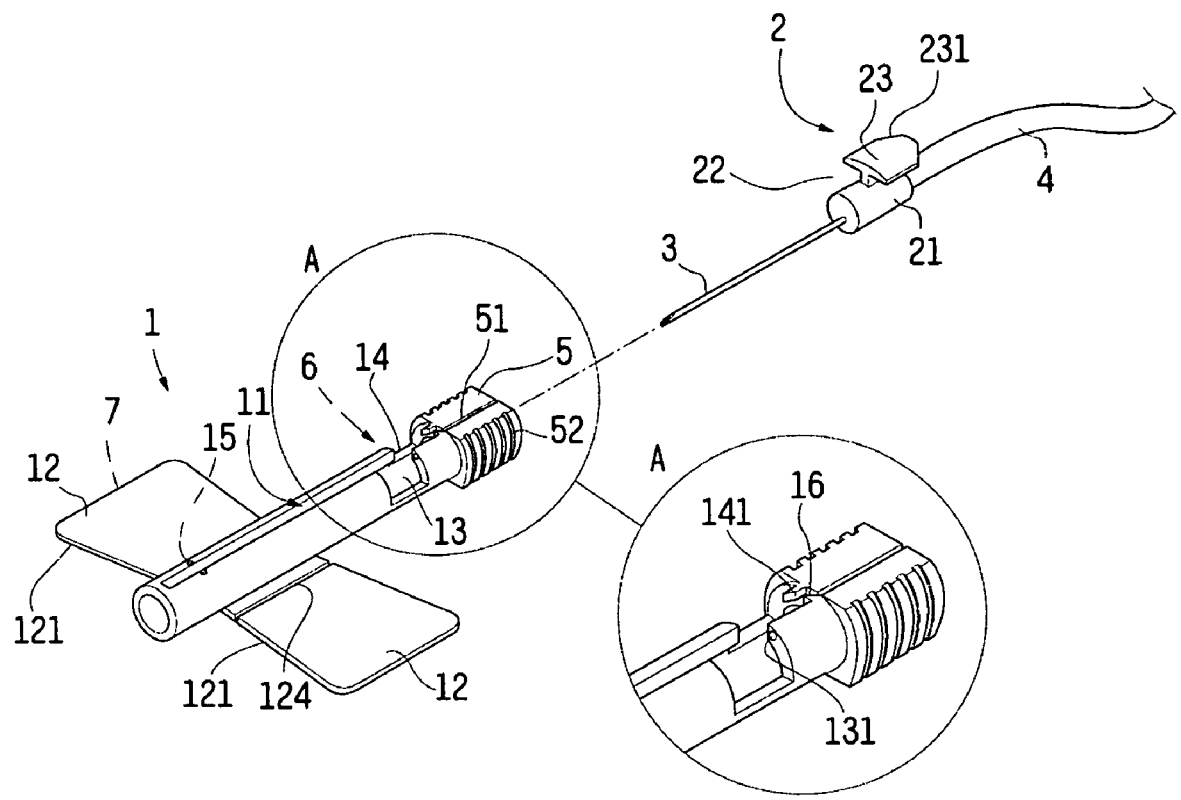
FIG. 1 is an exploded view of a safety winged needle structure in accordance with the present invention.
Figure 2:
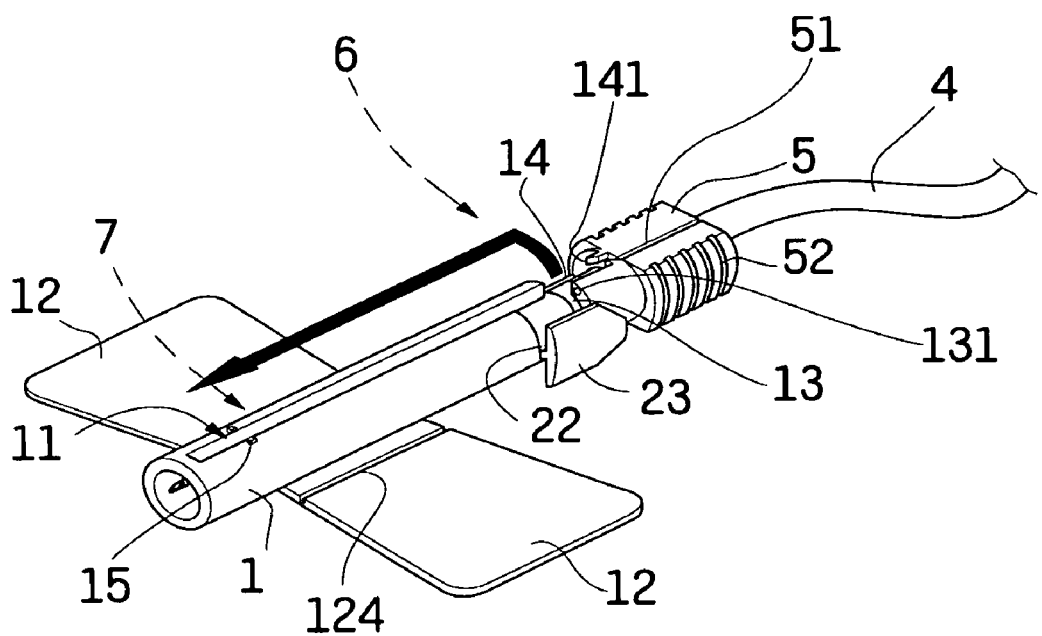
FIG. 2 is a perspective view of a safety winged needle structure in accordance with the present invention.
Figure 3:
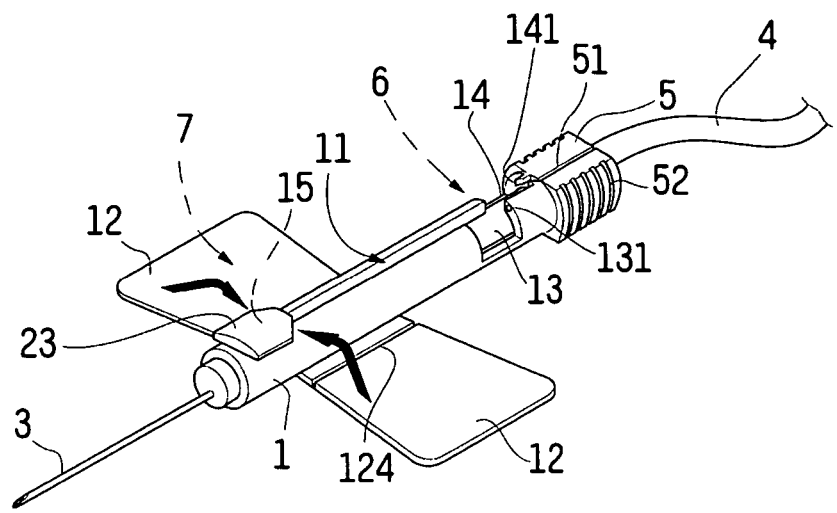
FIG. 3 is a perspective view of a safety winged needle structure with its accommodating body being pushed out in accordance with the present invention.

Referring to FIGS. 1 to 6, a safety winged needle structure of the invention comprises the following elements:

A protective casing 1 includes a sliding slot 11 disposed on a sidewall of the protective casing 1 and extended from an end of the protective casing 1 to another end of the protective casing 1 and sequentially having a first position 6 where the needle is shielded and a second position 7 where the needle is exposed, a positioning embossed dot 15 disposed separately on both sides of the sliding slot 11 on a corresponding wall of the protective casing 1, a stop portion 16 disposed on the sliding slot 11, and a base assembly portion 5 disposed on an end of the protective casing 1, wherein the sidewall of the base assembly portion 5 includes at least one breach 51 penetrated through the base assembly portion 5 and interconnected with the sliding slot 11, a plurality of slippery resisting lines 52 disposed on at least one lateral surface of the base assembly portion 5, and two wings 12 extended separately from both sides of the sliding slot 11 of the sidewall of the protective casing 1, and the wing 12 is substantially in a fan-shape and extended in a direction opposite from the protective casing 1 and forming a holding portion 125 on the surface of the wing 12, and the wing 12 has a folded line 124 disposed proximate to a surface of the protective casing 1 and parallel to the protective casing 1. At least one of the two wings has the first positioning portion which is used to fix (shut-off) the push portion, so the push portion does not withdraw during operation.

An accommodating body 2 is disposed in the protective casing 1, and a side of the accommodating body 2 has a sliding member 21 slidably disposed at the sliding slot 11, a neck portion 22 which is molded a surface of the sliding member 21 and protruded through the sliding slot 11, and a pushing portion 23. A top of the neck portion is a pushing portion 23.

A needle 3 is connected to an end of the sliding member 21, and the axis of the needle 3 is biased from the axis of the accommodating body 2, and another end of the accommodating body 2 is coupled to a tube.

The sliding slot 11 has a latch groove 13 and a latch groove 14 concavely disposed along a sidewall of the protective casing 1, and the latch groove 13 is situated at a lateral end of a first position 6 of the sliding slot 11 for accommodating the sliding member 21, and the latch groove 13 has an embossed dot 131. In the method of installing the accommodating body 2, the accommodating body 2 is inserted into a rear end of the protective casing 1, and the elasticity of a breach 51 of the base assembly portion 5 allows the accommodating body 2 to spread open the breach 51 and enter into the sliding slot 11.

The wall of the sliding slot 11 has a stop portion 16 for preventing the accommodating body 2 from falling out from the breach of the base assembly portion 5 again. Before the winged needle is used, the accommodating body 2 is accommodated into the corresponding latch groove 13 and positioned by the embossed dot 131. If the winged needle is used, it is necessary to rotate the pushing portion 23 of the accommodating body 2, so that the accommodating body 2 is separated from the embossed dot 131 of the latch groove 13 to allow the sliding member 21 to enter into the sliding slot 11, and move the sliding member 21 along the sliding slot 11 to the second position 7, and fix the positioning embossed dot 15 on the wall of the protective casing 1, and the needle 3 is exposed from the protective casing 1.

Figure 4:
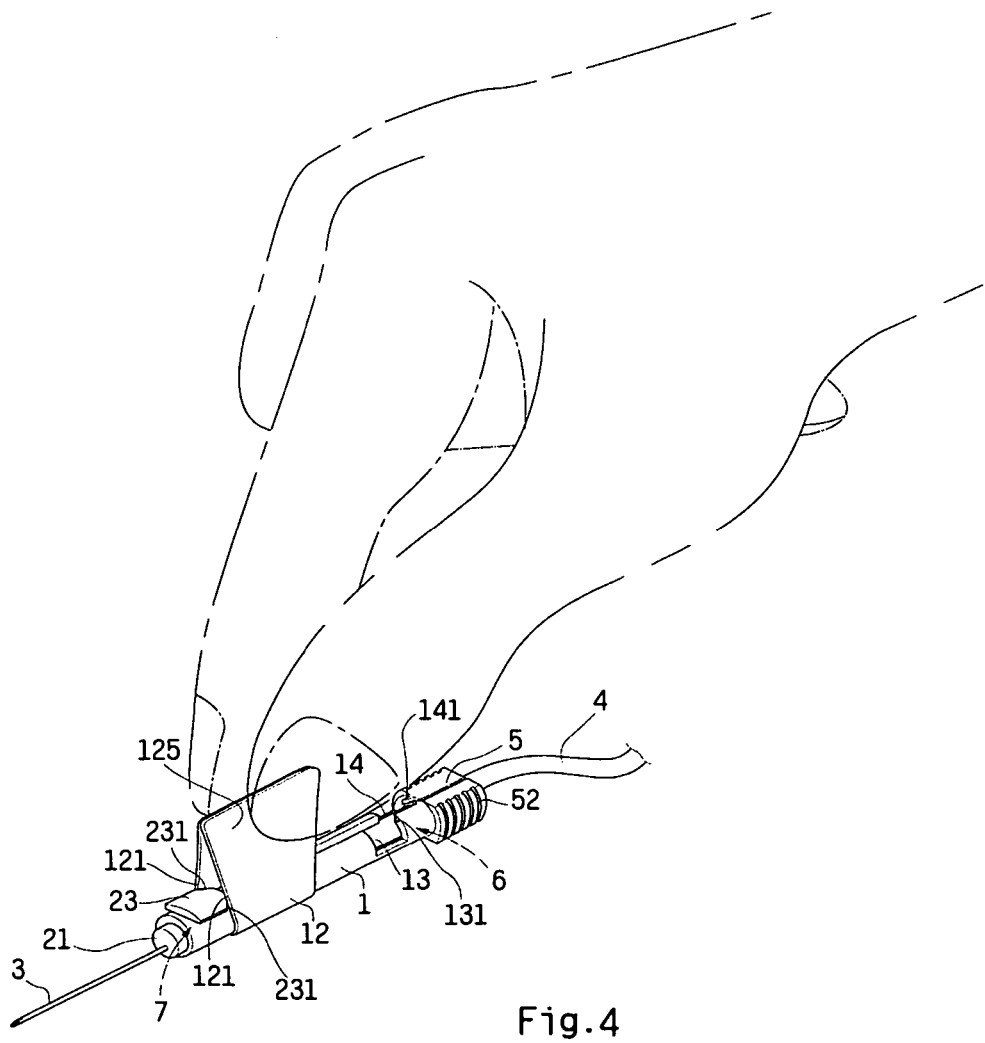
FIG. 4 shows an application of a safety winged needle structure of the present invention.

Referring to FIG. 4, the wing 12 is extended separately and laterally from both sides of the sliding slot 11 on the wall of the protective casing 1, and at least one wing 12 has the first positioning portion; wherein the first positioning portion is the anterior edge of the wing 12, and a second positioning portion is the posterior part of the pushing portion 23, such that when the sliding member 21 is moved along the sliding slot 11 to the second position 7, the two wings 12 are lifted and folded to both sides of the sliding slot. Under this situation, the first positioning portions is behind a second positioning portion which posterior part is fixed (shut-off) as well as the sliding member can not be withdrawn.

Figure 5:
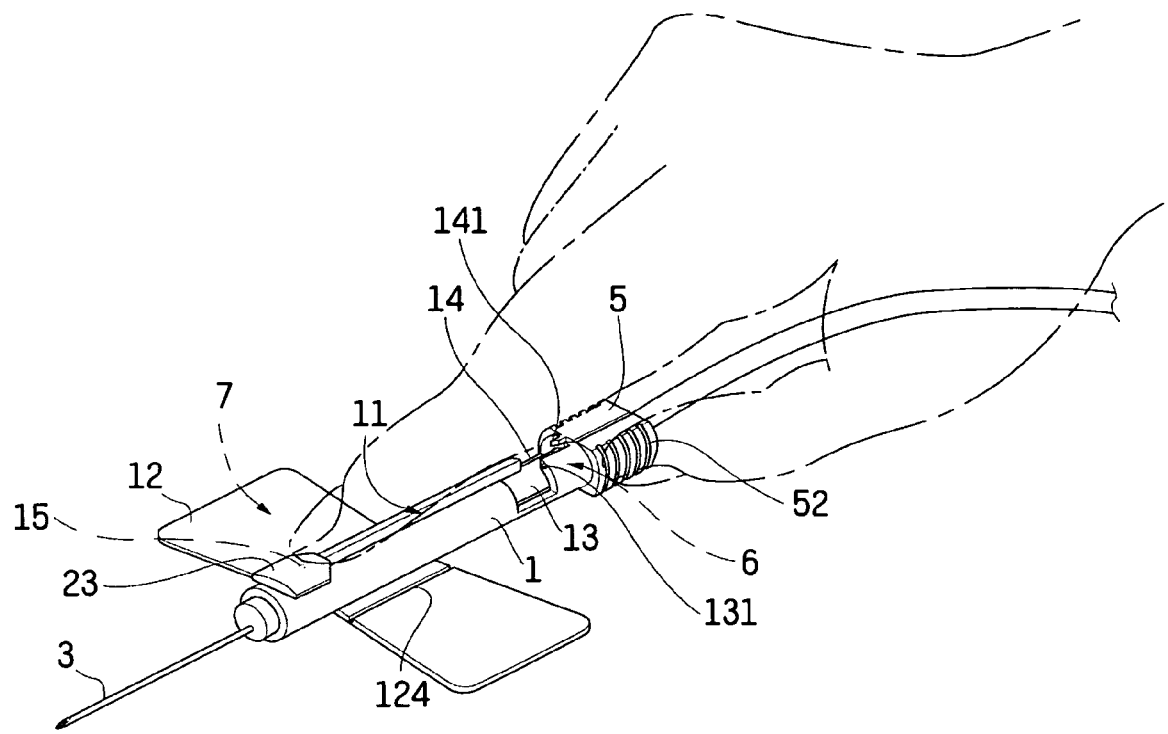
FIG. 5 shows another application of a safety winged needle structure of the present invention.
Figure 6:
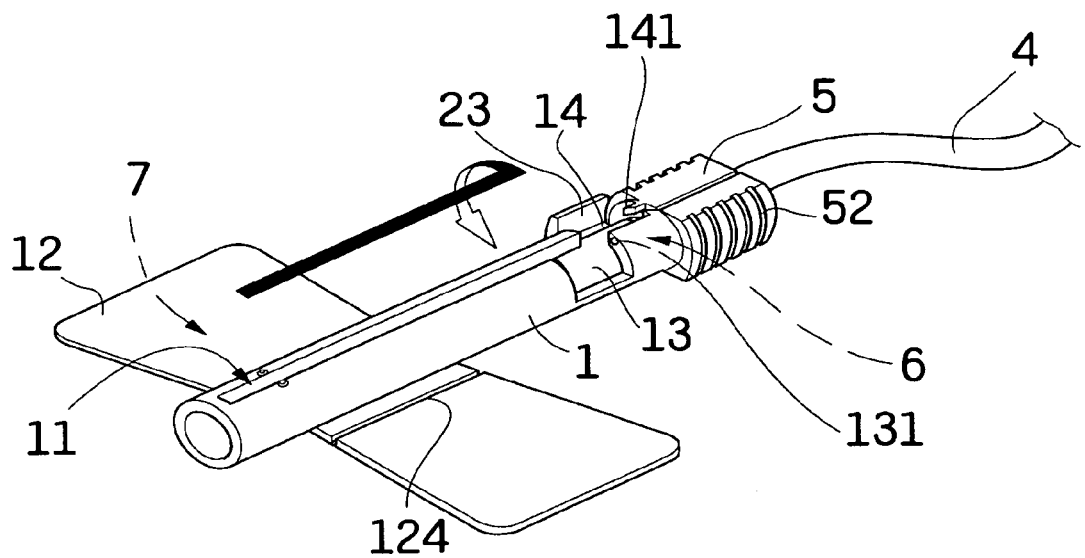
FIG. 6 is a perspective view of a safety winged needle structure with its accommodating member being pushed back in accordance with the present invention.
Figure 7:
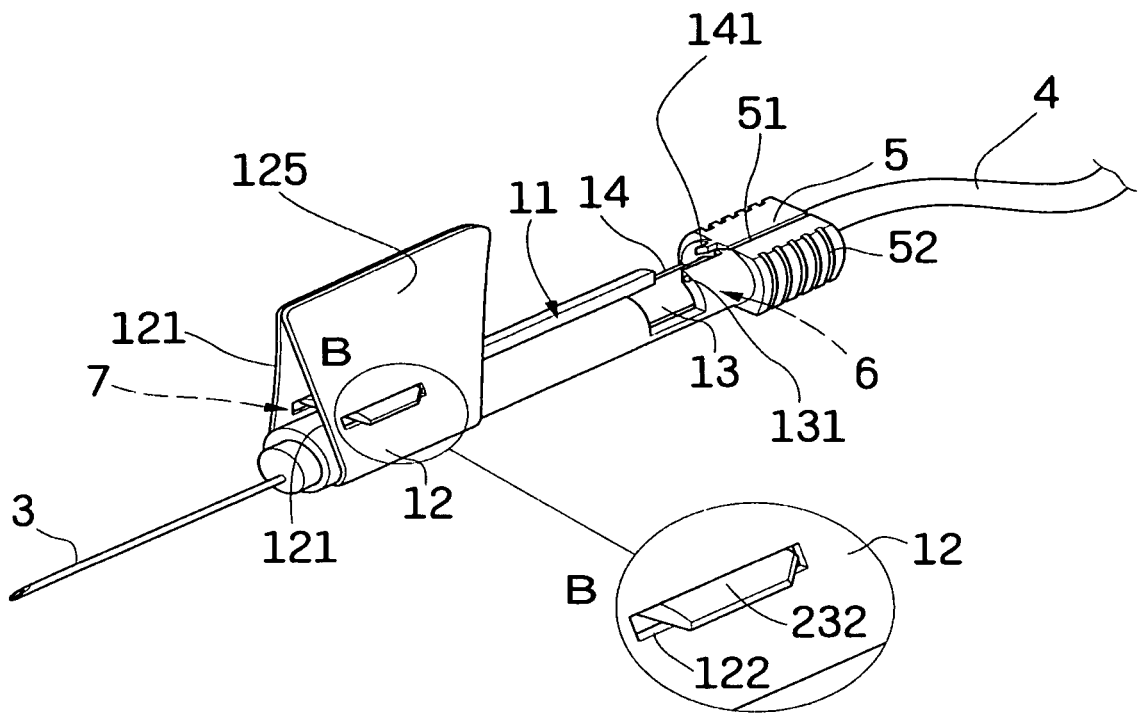
FIG. 7 is a perspective view of a safety winged needle structure in accordance with a second preferred embodiment of the present invention.

Referring to FIGS. 5 and 6, medical professionals are required to complete the aforementioned injection by one hand for preventing unintentional contacts of the needle 3 or infections to them. Medical professionals usually clamp the base assembly portion 5 by their thumb and middle finger and rotate the pushing portion 23 out from the latch groove 13 by their index finger, and then push the pushing portion 23 to slide the sliding member 21 along the sliding slot 11, so that when the sliding member 21 is moved along the sliding slot 11 to the second position 7, the needle 3 is exposed from the protective casing 1. After the winged needle is used, medical professionals push the sliding member 21 back to its original position by their index finger, such that the sliding member 21 is moved along the sliding slot 11 to the first position 6. When the sliding member 21 passes through the latch groove 13, the sliding member 21 is stopped by the embossed dot 131, and the sliding member 21 is prevented from entering the latch groove 13, so that medical professionals can push the sliding member 21 all the way to the bottom easily, so as to push the sliding member into the latch groove 14 and hide and store the needle 3 in the protective casing 1. Since the latch groove 14 has a stop member 141, therefore the sliding member 21 is prevented from fall out easily, and a second use of the winged needle is prevented effectively. Referring to FIG. 7 for a safety winged needle structure in accordance with the present invention, an insert opening 122 disposed on a surface of the wing 12 is the first positioning portion and a protruding tenon 232 at the pushing portion 23 is a second positioning portion. The insert opening 122 corresponds to protruding tenon 232. The lateral side dimension of insert opening 122 is larger than that of protruding tenon 232. (Enlarged view B) When the sliding member is moved along the sliding slot to the second position, both wings are lifted and folded to each sides of the sliding slot. Under this situation, the first positioning portions is behind a second positioning portion which posterior part is fixed as well as the sliding member can not be withdrawn. It means that one wing has the first positioning portion corresponding to the second positioning portion of the push portion.

Figure 8:
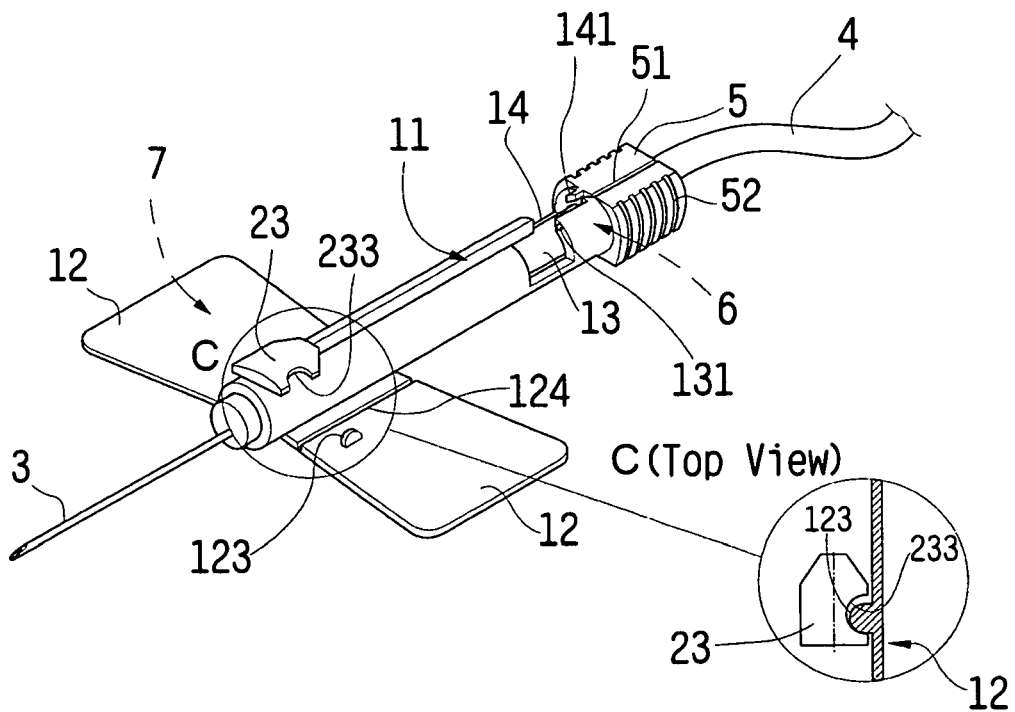
FIG. 8 is a perspective view of a safety winged needle structure in accordance with a third preferred embodiment of the present invention.
Figure 9:
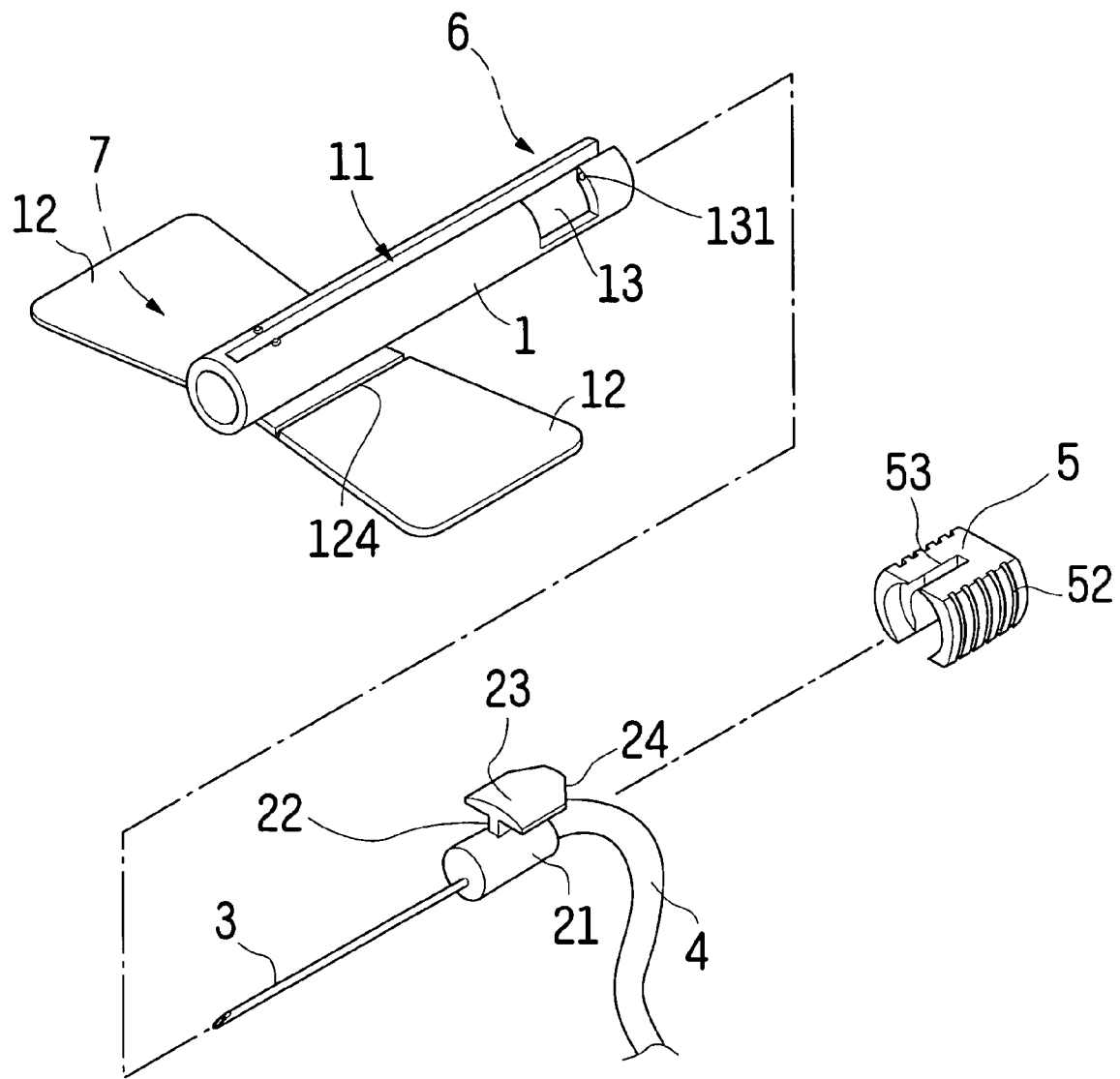
FIG. 9 is an exploded view of a safety winged needle structure in accordance with a fourth preferred embodiment of the present invention.
Figure 10:
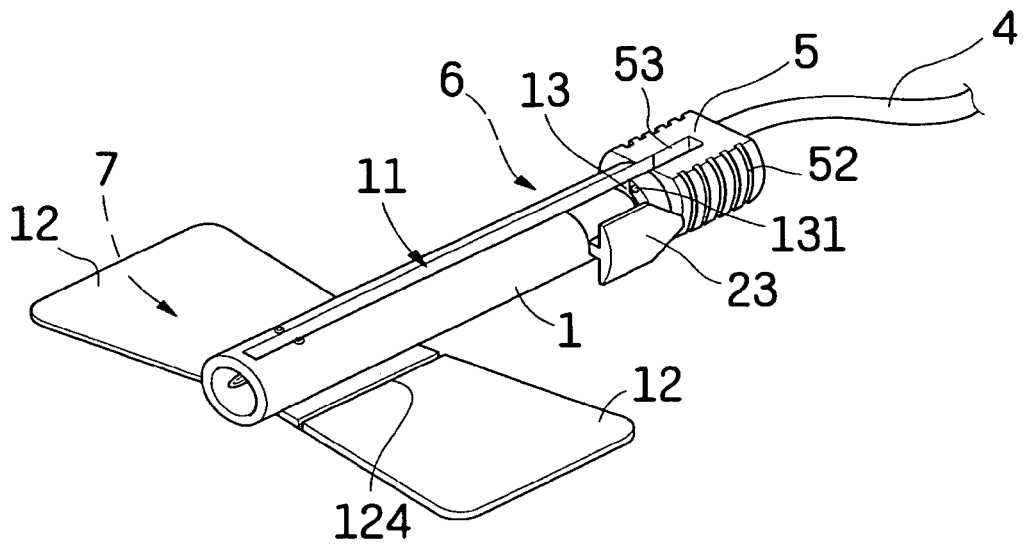
FIG. 10 is a perspective view of a safety winged needle structure in accordance with a fourth preferred embodiment of the present invention.
Figure 11:
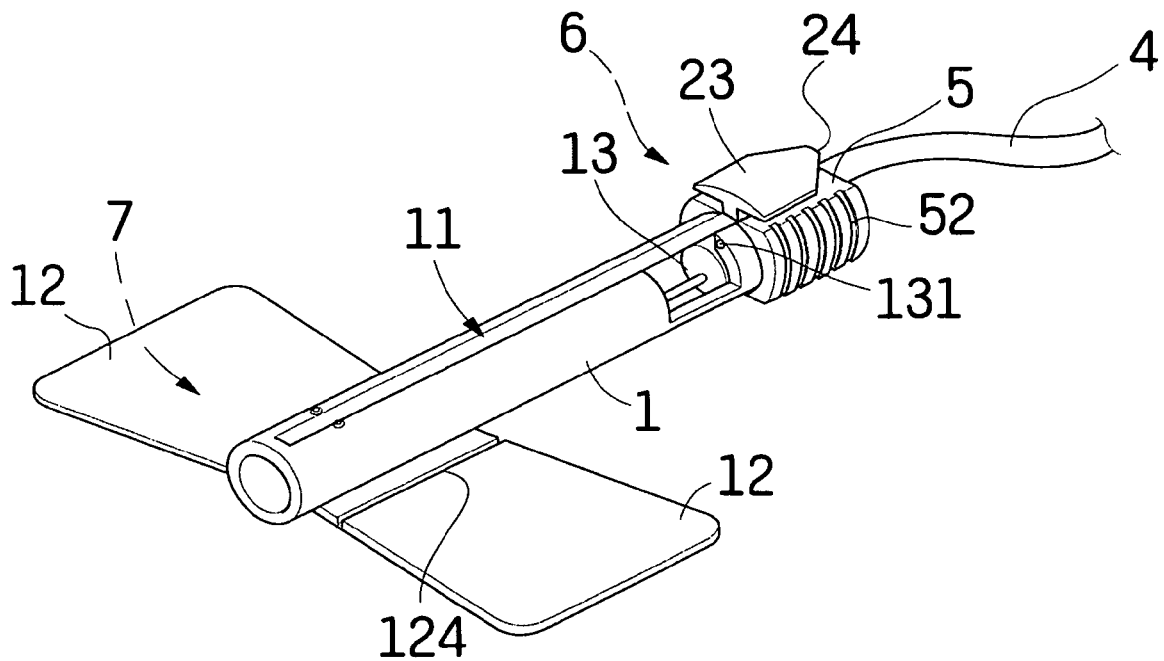
FIG. 11 shows a safety winged needle structure after its use in accordance with a fourth preferred embodiment of the present invention.
Figure 12:
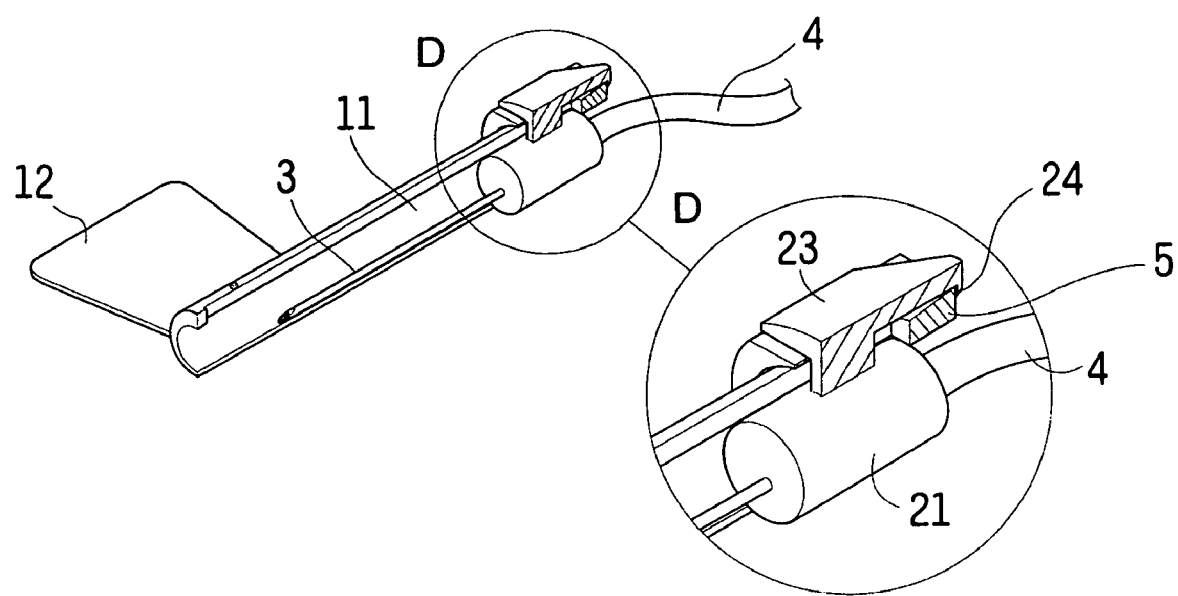
FIG. 12 is an enlarged view of a portion of a safety winged needle structure after its use in accordance with a fourth preferred embodiment of the present invention.

Referring to FIG. 8 for a safety winged needle structure in accordance with the present invention, a first positioning portion is an embossed dot 123 disposed on a surface of the wing 12, and a second positioning portion is a notch 233 disposed on the pushing portion 23, so that the embossed dot 123 (first positioning portions) blocks the notch 233 (second positioning portion) at its posterior part for positioning the sliding member 21, so as to prevent the winged needle from sliding backwards. (Enlarged View C). It means when the sliding member is moved along the sliding slot to the second position, both wings are lifted and folded to each sides of the sliding slot. Under this situation, the first positioning portion is behind a second positioning portion which posterior part is fixed as well as the sliding member can not be withdrawn.

Referring to FIGS. 9, 10, 11 and 12 for a safety winged needle structure that comes with a quick installation in accordance with the present invention, the base assembly portion 5 is in an inverted-U cylindrical shape and engaged with an end of the protective casing 1, such that a tube 4 at an end of the accommodating body 2 can be sheathed into the base assembly portion 5 easily, and the base assembly portion 5 has a sliding section 53 concavely disposed at an end of the corresponding sliding slot 11 and coupled to the sliding slot 11, for allowing the sliding member 21 to be entered slidably along the sliding slot 11, and the pushing portion 23 has a protruding latch 24.

After the winged needle is used, the sliding member 21 is retracted to the first position 6, and the protruding latch 24 of pushing portion 23 is latched securely with the base assembly portion 5 to fix the sliding member 21, so as to prevent the winged needle to be used by others for a second time. (Enlarged View D)

Figure 13:
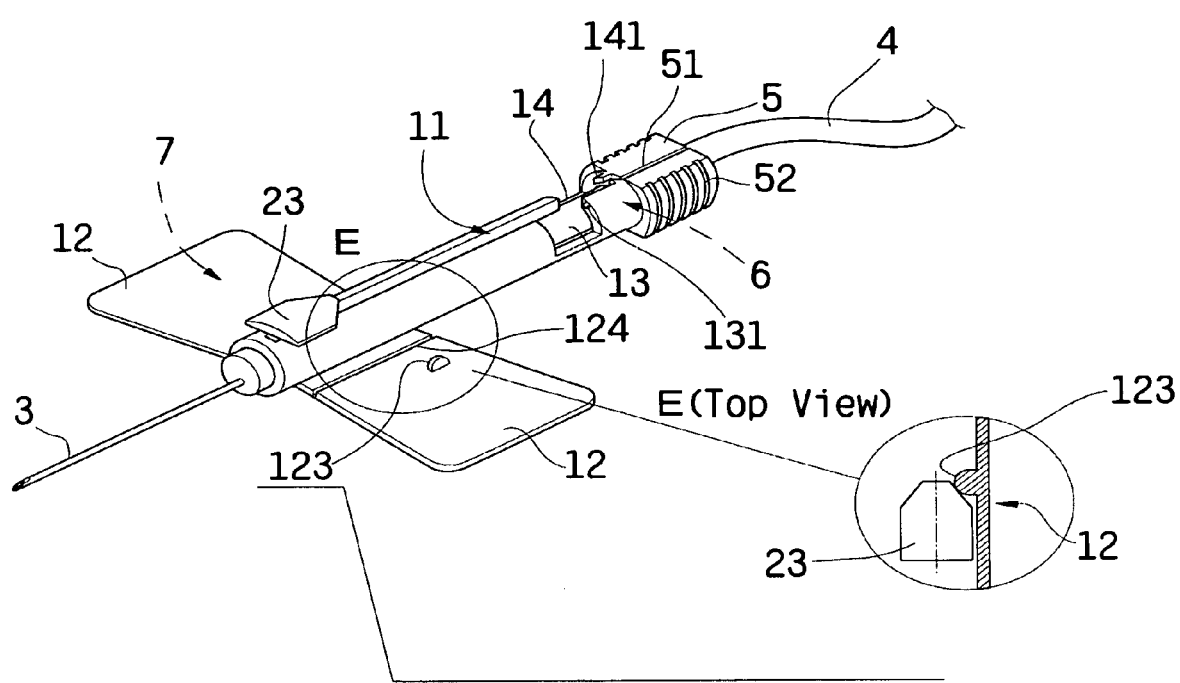
FIG. 13 is a perspective view of a safety winged needle structure in accordance with a fifth preferred embodiment of the present invention

Referring to FIG. 13 for a safety winged needle structure in accordance with the present invention, the first positioning portion is an embossed dot 123 disposed on a surface of the wing 12, and a second positioning portion is the posterior part of the pushing portion 23, such that the embossed dot 123 (first positioning portion) blocks the posterior part of the pushing portion 23 (second positioning portion) at its posterior part for blocking the sliding member 21, so as to prevent the winged needle from sliding backwards. (Enlarged Top View E) It means when the sliding member is moved along the sliding slot to the second position, both wings are lifted and folded to each sides of the sliding slot. Under this situation, the first positioning portions is behind a second positioning portion which posterior part is fixed as well as the sliding member can not be withdrawn.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety winged needle structure, comprising:
a protective casing and an accommodating body disposed in the protective casing,
the accommodating body having a sliding member slidably movable within the protective casing, a neck portion extending from the sliding member, and a pushing portion attached to the neck portion and defining a top of the accommodating body, the pushing portion including two sides, and wherein a needle is attached to the accommodating body,
the protective casing having at least one sliding slot disposed on a sidewall of the protective casing, a first position where the needle is shielded by the protective casing and a second position where the needle is exposed out of the protective casing, and two wings extending laterally from the protective casing, one of the wings having a first positioning structure, wherein the first positioning structure is a lateral edge of the wing;
wherein when the accommodating body is moved within the protective casing to the second position, the two wings are configured to be moved upwards to a side of the protective casing and are pinched together over the sliding slot, thereby positioning the first positioning structure behind the sides of the pushing portion and preventing the accommodating body from sliding back from the second position.

2. A safety winged needle structure, comprising:
a protective casing and an accommodating body disposed in the protective casing,
the accommodating body having a sliding member slidably movable within the protective casing, a neck portion extending from the sliding member, and a pushing portion attached to the neck portion and defining a top of the accommodating body, the pushing portion including a protruding tenon, and wherein a needle is attached to the accommodating body,
the protective casing having at least one sliding slot disposed on a sidewall of the protective casing, a first position where the needle is shielded by the protective casing and a second position where the needle is exposed out of the protective casing, and two wings extending laterally from the protective casing, one of the wings having a first positioning structure, wherein the first positioning structure is an opening through the wing;
wherein when the accommodating body is moved within the protective casing to the second position, the two wings are configured to be moved upwards to a side of the protective casing and are pinched together over the sliding slot, thereby positioning the protruding tenon within the opening thus preventing the accommodating body from sliding back from the second position.

3. A safety winged needle structure, comprising:
a protective casing and an accommodating body disposed in the protective casing,
the accommodating body having a sliding member slidably movable within the protective casing, a neck portion extending from the sliding member, and a pushing portion attached to the neck portion and defining a top of the accommodating body, the pushing portion including a notch, and wherein a needle is attached to the accommodating body,
the protective casing having at least one sliding slot disposed on a sidewall of the protective casing, a first position where the needle is shielded by the protective casing and a second position where the needle is exposed out of the protective casing, and two wings extending laterally from the protective casing, one of the wings having a first positioning structure, wherein the first positioning structure is an embossed dot protruding from the wing;
wherein when the accommodating body is moved within the protective casing to the second position, the two wings are configured to be moved upwards to a side of the protective casing and are pinched together over the sliding slot, thereby positioning the embossed dot within the notch thus preventing the accommodating body from sliding back from the second position.

* * * * *